(12) United States Patent
Berry et al.

(10) Patent No.: US 8,309,713 B2
(45) Date of Patent: Nov. 13, 2012

(54) PROCESS FOR THE PREPARATION OF 6-α,9-α-DIFLUORO-17-α-((2-FURANYLCARBONYL)OXY)-11-β-HYDROXY-16-α-METHY1-3-OXO-ANDROSTA-1,4-DIENE-17-β- -CARBOTHIOIC ACID S-FLUOROMETHYL

(75) Inventors: Malcolm Brian Berry, Stevenage (GB); Mark Jason Hughes, Stevenage (GB); David Parry-Jones, Stevenage (GB); Stephen John Skittrall, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 800 days.

(21) Appl. No.: 12/304,839

(22) PCT Filed: Jun. 13, 2007

(86) PCT No.: PCT/EP2007/055805
§ 371 (c)(1),
(2), (4) Date: Dec. 15, 2008

(87) PCT Pub. No.: WO2007/144363
PCT Pub. Date: Dec. 21, 2007

(65) Prior Publication Data
US 2009/0118495 A1    May 7, 2009

(30) Foreign Application Priority Data
Jun. 16, 2006    (GB) .................................. 0612027.3

(51) Int. Cl.
*C07J 31/00*    (2006.01)
(52) U.S. Cl. ....................................................... 540/114
(58) Field of Classification Search ................... 540/114
See application file for complete search history.

(56) References Cited

U.S. PATENT DOCUMENTS
4,335,121 A    6/1982    Phillipps et al.

FOREIGN PATENT DOCUMENTS
WO    0208243 A1    1/2002
WO    0212265 A1    2/2002

*Primary Examiner* — Brenda Coleman
(74) *Attorney, Agent, or Firm* — James P. Riek

(57) ABSTRACT

A novel process for preparing a compound of formula (I)

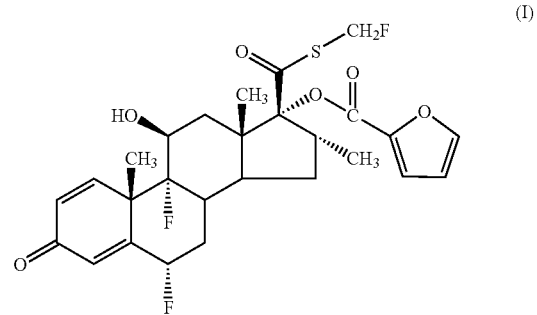

which comprises converting a compound of formula (II)

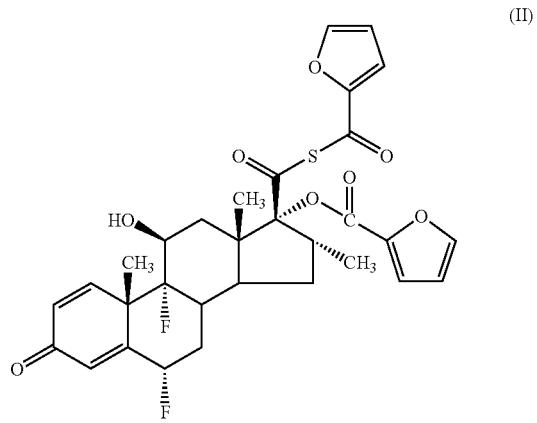

to a compound of formula (I) via a compound of formula (III), or a salt thereof,

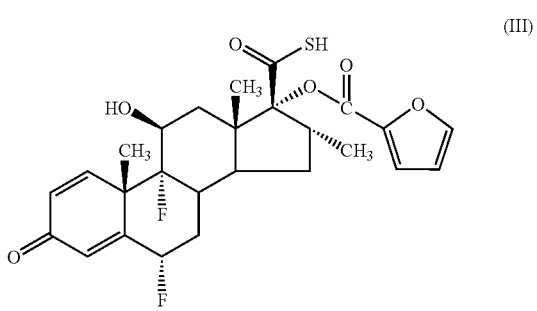

without isolating any intermediates.

24 Claims, No Drawings

PROCESS FOR THE PREPARATION OF 6-α,9-α-DIFLUORO-17-α-((2-FURANYLCARBONYL)OXY)-11-β-HYDROXY-16-α-METHY1-3-OXO-ANDROSTA-1,4-DIENE-17-β--CARBOTHIOIC ACID S-FLUOROMETHYL

This application is filed pursuant to 35 U.S.C. §371 as a U.S. National Phase Application of International Patent Application No. PCT/EP2007/055805 filed 13 Jun. 2007, which claims priority from GB Application No. 0612027.3 filed 16 Jun. 2006.

The present invention relates to a novel process for preparing a glucocorticoid.

Glucocorticoids which have anti-inflammatory properties are known and are widely used for the treatment of inflammatory disorders or diseases such as asthma and rhinitis. For example, U.S. Pat. No. 4,335,121 discloses 6α,9α-difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced, it remains an object of research to produce new molecules which have excellent anti-inflammatory properties, with predictable pharmacokinetic and pharmacodynamic properties, with an attractive side effect profile, and with a convenient treatment regime.

International Patent Application WO02/12265 discloses a novel glucocorticoid compound which substantially meets these objectives namely 6α,9α-difluoro-17α-[(2-furanylcarbonyl)oxy]-11β-hydroxy-16α-methyl-3-oxo-androsta-1,4-diene-17β-carbothioic acid S-fluoromethyl ester referred hereinafter as compound of formula (I):

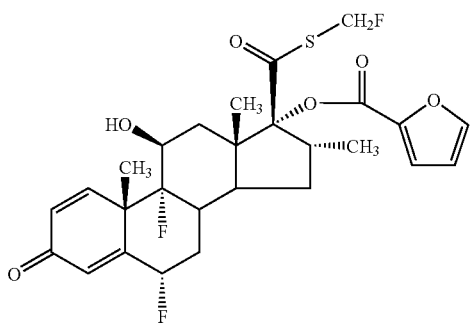

and a process/processes for preparing this compound in which intermediates are isolated.

Fluticasone propionate and a process for preparing it, including a process for preparing certain intermediates which are common with intermediates in the synthesis of a compound of formula (I) are described in U.S. Pat. No. 4,335,121.

WO02/08243 discloses processes for preparing intermediates useful in the preparation of fluticasone propionate and a compound of formula (I).

The object of the present invention is principally to provide a process for preparing a compound of formula (I) without isolating any intermediates.

Thus according to the invention there is provided a process for preparing a compound of formula (I) which comprises converting a compound of formula (II)

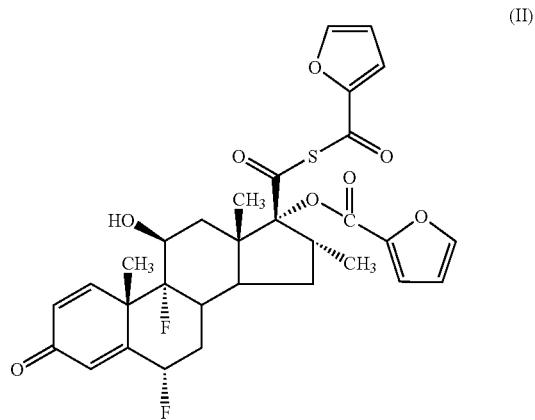

to a compound of formula (I) via a compound of formula (III), or a salt thereof,

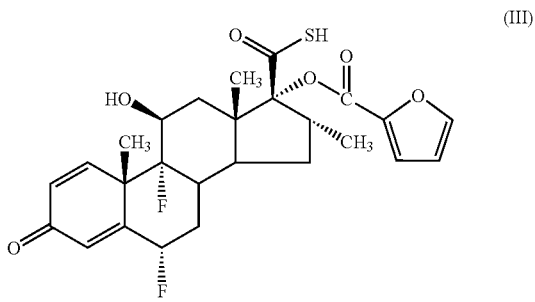

without isolating any intermediates. The process may be performed in a homogeneous solution.

In one aspect of the invention there is also provided a process for the preparation of compounds of formula (III) and its precursors.

In order to perform the process of synthesis of the compound of formula (I) from the compound of formula (II) without isolating any intermediates it is necessary to undertake the reactions in a solvent which is acceptable for all stages of the process. Examples of suitable solvents may include pentan-2-one, methylethylketone (MEK) and mixtures thereof. A particularly suitable solvent for use in the invention is methylethylketone (MEK). The advantage of MEK is that it provides suitable solubility of reagents and speed of reaction.

The conversion of a compound of formula (II) to a compound of formula (III) may be performed by employing a deprotecting reagent such as an amine base, thiol or alcohol, for example a primary or secondary amine or a molecule containing both secondary and tertiary amine bases, for example, N-methyl piperazine. The advantage of N-methyl piperazine is that the N-methyl piperazine-furoyl amide which is formed as a result of the process is readily soluble in water (especially as its hydrochloride (HCl) salt) and can therefore be removed from the reaction mixture during an aqueous work-up at the end of the process. The deprotection reaction is suitably performed at a temperature in the range of −10 to 10° C., especially −5 to 0° C. and is rapid, for example taking less than 15 minutes.

The prior art document WO02/12265 describes the use of N,N-diethylamine or N,N-diethanolamine as the deprotecting reagent reagent in ethyl acetate, methyl acetate or methanol as solvent. These reagents, although suitable in principle, yield by-products which are not so easily removed from the reaction mixture as they are less water soluble than the N-methyl piperazine-furoyl amide described above.

Progress of the conversion of the compound of formula (II) to the compound of formula (III) may be monitored using high performance liquid chromatography (HPLC).

Following conversion of the compound of formula (II) to the compound of formula (III), the latter compound may be further converted to the compound of formula (I) by reacting the compound of formula (III) with a fluoromethylating agent such as chlorofluoromethane (CFM) or bromofluoromethane (BFM), particularly bromofluoromethane (BFM). The reaction is performed in a solvent common with the earlier stage of converting a compound of formula (II) to a compound of formula (III), preferably MEK. Preferably BFM is employed as a solution in a solvent, especially MEK.

Suitably an excess of BFM is employed, for example, 1.2 equivalents. The BFM is added at a low temperature, for example 0° C., and the reaction mixture is then warmed to 15 to 60° C., for example 20 to 22° C. At higher temperatures, for example 50 to 60° C., the reaction time is relatively short, for example less than 30 minutes. At lower temperatures, for example 20 to 30° C., the reaction is considerably slower, for example taking 5 hours, but a slight improvement in quality is achieved by reducing the level of alkylation on the carbonyl oxygen rather than on sulphur.

The compound of formula (III) may be employed as a salt, such as an organic amine thiolate salt, for example a trialkylamine salt wherein the trialkylamine group is represented by $R^1R^2R^3N$ wherein each of $R^1$, $R^2$ and $R^3$ independently represents a $C_{3-6}$ straight or branched alkyl group. In one embodiment the organic amine thiolate salt of the compound of formula (III) is the tripropylamine or the tributylamine salt.

Progress of the conversion of the compound of formula (III) to the compound of formula (I) may be monitored using HPLC.

Once reaction with the fluoroalkylating agent is complete, the excess reagent may be quenched or removed. In one method, the fluoroalkylating agent is quenched with a chemical quenching agent i.e. a chemical reagent that reacts with the fluoroalkylating agent to produce an unreactive substance. For this purpose, compounds having strongly nucleophilic functionality, for example, thiol compounds are suitable. Hence N,N-diethylaminoethane thiol is a suitable reagent for quenching BFM. In another method, the excess reagent can be removed by distillation.

The compound of formula (I) resulting from the aforesaid process can be purified using conventional extraction processes. Generally the compound of formula (I) is extracted into a solvent in which it has adequate solubility when blended with MEK and, more importantly, which is relatively immiscible with aqueous media, for example, dilute acids and bases, with which it may be washed to extract water soluble impurities. A particularly suitable extraction solvent for use in the process of the invention is methylisobutylketone (MIBK). Thus in one embodiment the solution of the compound of formula (I) resulting from the aforesaid process may be diluted with an excess quantity of MIBK thereby to extract the compound of formula (I) into MIBK. This solution may then be worked up and washed in a conventional manner with successive washes of aqueous components, such as, aqueous acid, for example, dilute aqueous HCl, aqueous base, for example, dilute aqueous potassium carbonate and water.

Once the washed MIBK fraction (which contains the compound of formula (I)) is separated from the aqueous fraction, it may suitably be distilled in order to remove any remaining water and excess fluoroalkylating agent, for example BFM. A proportion of the MEK is also removed during distillation.

The compound of formula (I) in solid form may be prepared by precipitating the solid from a solution by addition of an anti-solvent. A suitable solvent is a mixture of MEK/MIBK, for example in the ratio of 1:9 v/v, and a suitable anti-solvent is n-heptane. In one method, the solvent may be evaporated from the previously formed solution to yield a solid and a solution of the correct composition made up again (e.g. made up again in a mixture of MEK/MIBK 1:9 v/v). Alternatively the distillation process previously mentioned may be concluded at the stage when the ratio of MEK/MIBK reaches the appropriate level e.g. 1:9 v/v. Addition of n-heptane as anti-solvent dropwise over an extended period, for example 2 hours, at ambient temperature or slightly above, for example a temperature of approximately 30 to 35° C., leads to precipitation of the compound of formula (I). The suspension may then be cooled and the product collected by filtration.

The precipitation is suitably initiated by seeding with one or more crystals of the compound of formula (I).

The above mentioned ratio of MEK/MIBK 1:9 v/v is advantageous since it reflects a balance between having a sufficient proportion of MEK to enhance solubility of the compound of formula (I) in the solvent and not having too high a proportion which would lead to generation of an MEK solvate of the compound of formula (I) upon crystallisation.

The compound of formula (II) may be prepared by a process which comprises reacting a compound of formula (IV)

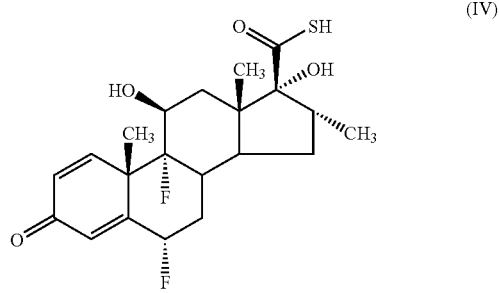

(IV)

or a salt thereof, for example the thiolate salt, with an activated 2-furoic acid derivative. The process may be performed in a homogeneous solution.

Examples of activated 2-furoic acid derivatives include halides and mixed anhydrides formed from 2-furoic acid. In one embodiment, the reagent is 2-furoyl chloride (hereinafter "furoyl chloride"). This reagent may be employed without additional solvent.

Suitable solvents for this reaction may include ethyl acetate (EtOAc), MEK, pentan-2-one and MIBK, for example, MEK, pentan-2-one and mixtures thereof. This reaction may be performed in the same solvent as the successive step. Thus the solvent may be MEK.

Without being limited by theory it is believed that the 17-α-furoyl ester of the compound of formula (III) is formed via a kinetically favoured 5-exo-trigonal intramolecular S—O acyl transfer, which then goes on to react with a further mole of the furoic acid derivative to produce the compound of formula (II) (the difuroate). In one embodiment, more than 2 molar equivalents of the activated 2-furoic acid derivative are employed per mole of compound of formula (IV), for example, around 2.2 molar equivalents. The reaction may be performed below 0° C., such as in the range of −10 to 0° C., for example −5 to 0° C. In another embodiment 4-dimethylaminopyridine (DMAP) is additionally employed to accelerate the intermolecular acylation between a compound of formula (II) and a compound of formula (IV), allowing less than 2.2 equivalents of furoyl chloride to be used, for example 1.5 equivalents.

The compound of formula (II) may be prepared from the compound of formula (IV) i.e. the compound of formula (II) is not isolated before ongoing processing to the compound of formula (I) via the compound of formula (III).

Progress of the conversion of the compound of formula (IV) or a salt thereof to the compound of formula (II) may be monitored using HPLC.

Compounds of formula (IV) may be prepared as described in GB 2,137,206A.

The compound of formula (IV) may be employed in the reaction in the form of a thiolate salt which is more reactive than the parent thioacid.

Suitable salts are salts formed with organic amines, for example, tertiary amines especially tripropylamine. The salt of compound of formula (IV) with tripropylamine (TPA) is very soluble in MEK. Furthermore tripropylamine hydrochloride (TPA.HCl) which is formed as a result of the reaction of the compound of formula (IV) with furoyl chloride is also very soluble in MEK. In one embodiment, the salt of the compound of formula (IV) is the TPA salt.

Salts of the compound of formula (IV) may be produced by reacting the compound of formula (IV) with the base, for example the organic amine such as TPA, in the prevailing solvent for example, MEK. This may typically be performed between 5° C. and ambient temperature.

The compound of formula (IV) may be employed as a salt, such as an organic amine thiolate salt, such as a trialkylamine salt wherein the trialkylamine group is represented by $R^1R^2R^3N$ wherein each of $R^1$, $R^2$ and $R^3$ independently represents a $C_{3-6}$ straight or branched alkyl group. In one embodiment the organic amine thiolate salt of the compound of formula (IV) is the tripropylamine or the tributylamine salt.

As mentioned above, progression of reactions may be monitored using HPLC. This technique may be used to ensure that the reaction has gone to completion and that the level of impurities generated conforms to specification. HPLC techniques may be performed in a conventional manner.

Control of temperature where heating or cooling is required, for example where reactions are exothermic, may be achieved through appropriate jacketing and heat exchange.

As described in the examples, the overall conversion of a compound of formula (IV) to a compound of formula (I) can be performed in a very efficient process. All stages from the compound of formula (IV) to the compound of formula (I) may be performed as a batch process.

The invention will now be illustrated by the following example.

EXAMPLE

Abbreviations

| MEK | methyethylketone (2-butanone) |
| MIBK | methylisobutylketone |
| HPLC | high performance liquid chromatography |
| wrt | with respect to |
| TPA | tripropylamine |
| BFM | bromofluoromethane |
| DMAP | 4-dimethylaminopyridine |
| eq | equivalents |

Example 1

Synthetic method for the synthesis of 6α,9α-difluoro-17α-[(2-furanylcarbonyl)oxy]-11β-hydroxy-16α-methyl-3-oxo-androsta-1,4-diene-17β-carbothioic acid S-fluoromethyl ester

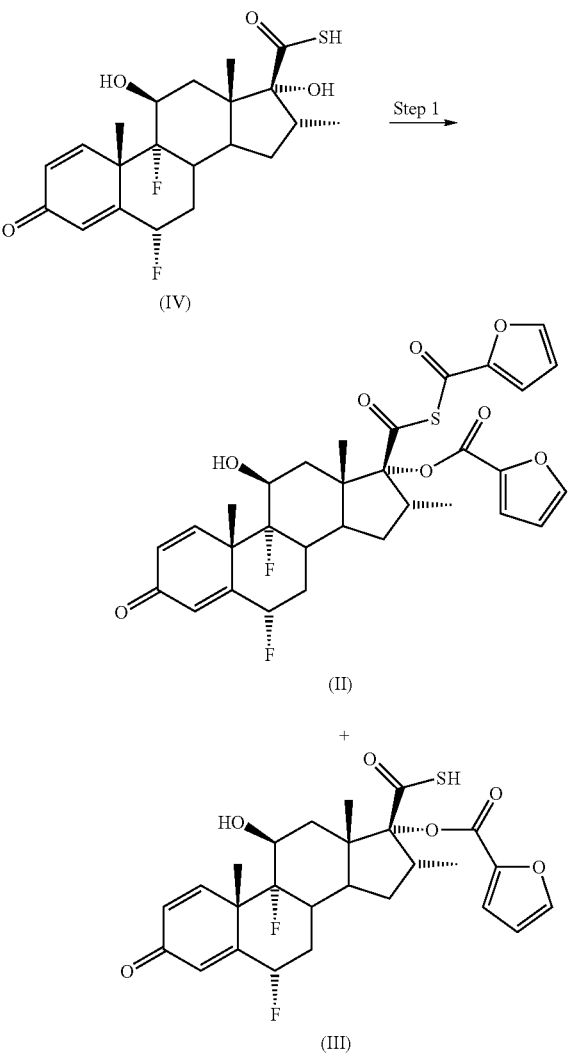

Step 1: 6α,9α-difluoro-11β,17α-dihydroxy-16α-methyl-3-oxo-androsta-1,4-diene-17β-carbothioic acid (compound of formula (IV), the thioacid) (10 g) and DMAP (0.296 g, 0.1 eq wrt the thioacid) were dissolved in MEK (120 ml, 8% w/v) by stirring at 20-22° C. under nitrogen for 10 minutes. Tripropylamine (14.3 ml, 3.1 eq wrt the thioacid) was then added as a single charge and the resulting solution cooled to between −8 to −5° C. Neat furoyl chloride (3.59 ml, 1.5 eq wrt the thioacid) was then added dropwise over 2-3 minutes at −5 to 0° C. and the reaction mixture stirred for a total of 15 minutes at −5 to 0° C. (HPLC indicated that <0.5% of the thioacid of formula (IV) remained).

-continued

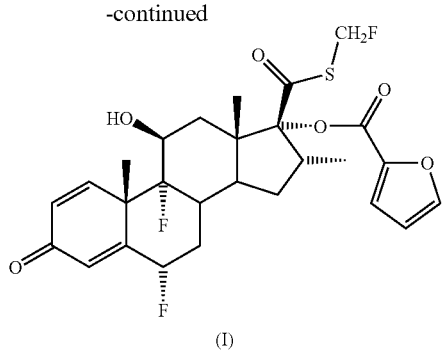

(I)

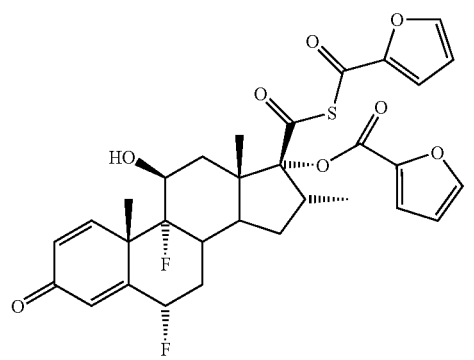

(II)

Step 3: A solution of bromofluoromethane (3.28 g, 1.2 eq wrt the thioacid) in MEK (10 ml, 32.8% w/v) was then added rapidly as a single charge at 0° C. The solution was then warmed rapidly to 20-22° C. and stirred for a total of 5 hours at 20-22° C. (HPLC indicated that no thioacid furoate (compound of formula (III)) remained).

The reaction mixture was then diluted with MIBK (230 ml) and washed subsequently with aqueous 2M hydrochloric acid (2×50 ml); water (1×50 ml); aqueous potassium carbonate (4% w/v, 1×30 ml) and then water (1×30 ml). The final organic phase was then concentrated under reduced pressure to give a fine off-white solid (13.01 g, 99.3% theoretical yield after correction for MIBK, 97.43% purity).

The invention claimed is:
1. A process for preparing a compound of formula (I)

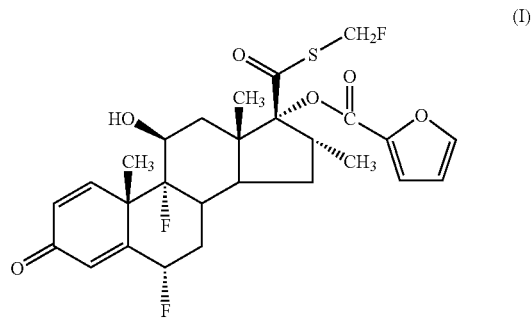

(I)

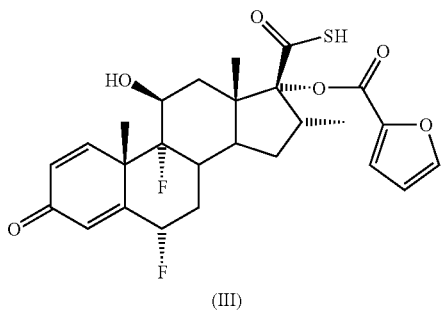

(III)

Step 2: A solution of N-methylpiperazine (1.62 ml, 0.6 eq wrt the thioacid) in water (4.8 ml, 30.5% w/v) was then added dropwise over 2-3 minutes at −5 to 0° C. and the reaction mixture stirred for a total of 10 minutes at −5 to 0° C. (HPLC indicated that <0.1% of the difuroate (compound of formula (II)) remained).

which comprises converting a compound of formula (II)

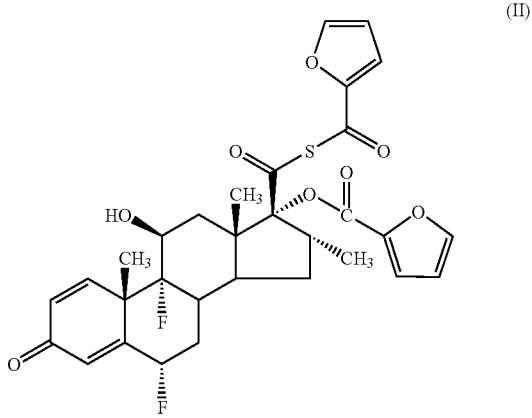

(II)

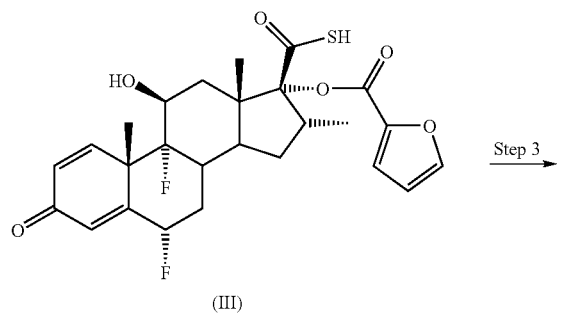

(III)

to a compound of formula (I) via a compound of formula (III), or a salt thereof,

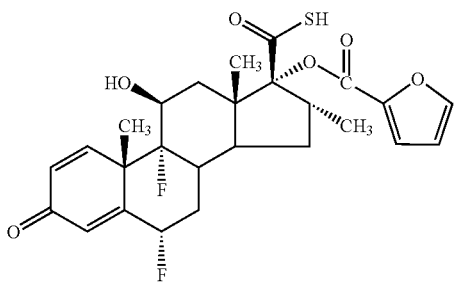

without isolating any intermediates, and wherein the process is performed in methyethylketone or pentan-2-one or mixtures thereof.

2. A process according to claim 1, wherein the process is performed in methyethylketone as solvent.

3. A process according to claim 1 wherein the compound of formula (II) is converted to the compound of formula (III) by reaction with a deprotecting agent which is an amine base, thiol or alcohol.

4. A process according to claim 3 wherein the amine base is a primary or secondary amine.

5. A process according to claim 4 wherein the amine base is N-methylpiperazine.

6. A process according to claim 1, wherein the compound of formula (II) is converted to a compound of formula (I) via an organic amine thiolate salt of the compound of formula (III).

7. A process according to claim 6 wherein the organic amine thiolate salt is a trialkylamine salt wherein the trialkylamine group is represented by $R^1R^2R^3N$ wherein each of $R^1$, $R^2$ and $R^3$ independently represents a $C_{3-6}$ straight or branched alkyl group.

8. A process according to claim 7 wherein the organic amine thiolate salt is the tripropylamine or the tributylamine salt.

9. A process according to claim 1 wherein the compound of formula (III) is converted to a compound of formula (I) by reaction with a fluoromethylating agent.

10. A process according to claim 9 wherein the fluoromethylating agent is bromofluoromethane.

11. A process according to claim 10 wherein bromofluoromethane is employed as a solution in methyethylketone.

12. A process according to claim 10 wherein the reaction mixture is treated with a chemical quenching agent to remove excess bromofluoromethane after reaction is complete.

13. A process according to claim 10 wherein after reaction the reaction mixture is extracted into methylisobutylketone by a process comprising dilution with methylisobutylketone.

14. A process according to claim 13 wherein after extraction into methylisobutylketone the solution is worked up and washed with one or more aqueous components.

15. A process according to claim 14 wherein the aqueous components comprise an aqueous acid and an aqueous base and water.

16. A process according to claim 13, wherein the methylisobutylketone solution is distilled to remove excess bromofluoromethane and water.

17. A process for preparation of a compound of formula (I) according to claim 1, wherein the compound of formula (II) is prepared by a process which comprises reacting a compound of formula (IV)

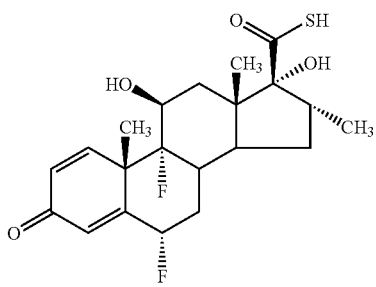

or a salt thereof
with an activated 2-furoic acid derivative, wherein said activated 2-furoic acid derivative is a halide or mixed anhydride formed from 2-fuoic acid, and said process is performed without isolating any intermediates.

18. A process according to claim 17 wherein the reaction is performed in pentan-2-one, methyethylketone or mixtures thereof as solvent.

19. A process according to claim 18 wherein the reaction is performed in methyethylketone as solvent.

20. A process according to claim 17, wherein the activated 2-furoic acid derivative is 2-furoyl chloride.

21. A process according to claim 17, wherein 4-dimethylaminopyridine is additionally employed.

22. A process according to claim 17, wherein the compound of formula (IV) is used as an organic amine thiolate salt.

23. A process according to claim 22 wherein the organic amine thiolate salt is a trialkylamine salt wherein the trialkylamine group is represented by $R^1R^2R^3N$ wherein each of $R^1$, $R^2$ and $R^3$ independently represents a $C_{3-6}$ straight or branched alkyl group.

24. A process according to claim 23 wherein the organic amine thiolate salt is the tripropylamine or the tributylamine salt.

* * * * *